United States Patent [19]

Morgan et al.

[11] Patent Number: 5,222,492
[45] Date of Patent: Jun. 29, 1993

[54] CARDIAC DEFIBRILLATOR INCLUDING AN ELECTRONIC ENERGY TRANSFER CIRCUIT

[75] Inventors: Carlton B. Morgan, Bainbridge Island; Daniel Yerkovich, Seattle, both of Wash.

[73] Assignee: Physio-Control Corporation, Redmond, Wash.

[21] Appl. No.: 790,238

[22] Filed: Nov. 8, 1991

[51] Int. Cl.[5] .................................. A61N 1/39
[52] U.S. Cl. ................................. 128/419 D
[58] Field of Search ...................... 128/419 D

[56] References Cited

U.S. PATENT DOCUMENTS

| | | | |
|---|---|---|---|
| 3,258,013 | 6/1966 | Druz | 128/419 D |
| 3,547,108 | 12/1970 | Seiffert | 128/419 D |
| 3,706,313 | 12/1972 | Milani et al. | 128/419 D |
| 3,782,389 | 1/1974 | Bell | 128/419 D |
| 3,814,105 | 6/1974 | Howard et al. | 128/419 D |
| 3,952,750 | 4/1976 | Mirowski et al. | 128/419 D |
| 4,106,494 | 8/1978 | McEachern | 128/419 D |
| 4,823,796 | 4/1989 | Benson | 128/419 D |
| 4,825,871 | 5/1989 | Cansell | 128/419 D |
| 4,926,862 | 5/1990 | Miyajima et al. | 128/419 D |

Primary Examiner—William E. Kamm
Attorney, Agent, or Firm—Christensen, O'Connor, Johnson & Kindness

[57] ABSTRACT

An energy transfer circuit (40) for delivering a cardiac defibrillation pulse to a patient (50). An energy storage capacitor (16) is coupled to a pair of electrodes (52a, 52b) through an electronic switch (42). The electronic switch is controlled by a control circuit (20). A current shunt 56 is connected in parallel with a pair of defibrillation electrodes (52a, 52b) to divert a leakage current that flows through the electronic switch away from the patient when a defibrillation pulse is not being delivered. A current sensor (64) or a voltage sensor (72) provide a feedback signal to the control circuit to regulate the energy of the defibrillation pulse that flows through the patient.

21 Claims, 8 Drawing Sheets

CARDIAC DEFIBRILLATOR INCLUDING AN ELECTRONIC ENERGY TRANSFER CIRCUIT

FIELD OF THE INVENTION

The present invention relates to energy transfer circuits in general and, in particular, to an energy transfer circuit for use in a cardiac defibrillator that includes a solid state switch and a current shunt to divert leakage current of the switch away from a pair of defibrillation electrodes.

BACKGROUND OF THE INVENTION

One of the most common and life-threatening heart irregularities is ventricular fibrillation in which the heart is unable to pump a significant volume of blood. When such an irregularity occurs, serious brain damage and death will invariably result unless a normal heart rhythm can be restored within a few minutes. Ventricular fibrillation can occur as a result of a heart attack but may also be caused by accidental electric shock or due to severe stress, such as may accompany surgery, drowning or the like.

The most effective treatment for restoring a normal rhythm to a heart muscle experiencing ventricular fibrillation is the application of a strong electric shock to the victim using a cardiac defibrillator. Cardiac defibrillators are medical devices for producing and delivering such shocks and have been successfully used for many years.

Conventional external cardiac defibrillators accumulate an electric charge on a storage capacitor and, when a switching mechanism is closed, transfer the stored energy in the form of a large current pulse to a patient. The switching mechanisms used in most defibrillators comprise heavy-duty electro-mechanical relays. Typically, the relays are responsive to a discharge control signal that actuates the relay to complete an electrical circuit between the storage capacitor, a waveshaping network, and a pair of defibrillation electrodes attached to the patient.

The cardiac defibrillation pulse, which is delivered to the patient by an energy transfer circuit that includes a electro-mechanical relay, generally comprises a single pulse having a damped sinusoidal shape that starts when the relay closes. Alternately, a cardiac defibrillation pulse may have an exponential shape that starts when the relay contact closes and stops when the relay contact opens. However, it has been found that other types of defibrillation currents may be more effective in terminating ventricular fibrillation. For example, it may be beneficial to apply a series of cardiac defibrillation current pulses to the patient in rapid succession, or it may be beneficial to maintain the magnitude of the defibrillation current flowing through the patient at a specific level. The use of electro-mechanical relays in an energy transfer circuit do not allow such types of defibrillation currents to be applied to the patient because the relay contacts cannot be switched closed and open fast enough. This slow response time does not allow the use of feedback signals obtained from the patient to be used in controlling the amount of energy delivered. Therefore, what is needed is an energy transfer circuit that can replace the electro-mechanical relays with a fast acting solid state switching device.

The problem with using solid-state switching devices in a cardiac defibrillation circuit is that such devices allow a certain amount of leakage current to flow even when the devices are in a nonconducting state. Heretofore, safety reasons have made it impractical to use solid-state circuitry devices in a cardiac defibrillator circuit without the additional isolation of electro-mechanical relays.

Therefore, it is desirable to provide an energy transfer circuit that employs a solid state switch in combination with a current shunt which can divert the leakage current away from the patient electrodes until a defibrillation pulse is delivered to the patient.

It is also desirable to provide an energy transfer circuit including a feedback control to regulate the delivery of a cardiac defibrillation pulse to the patient.

Finally, it is desirable to provide an energy transfer circuit that can deliver predetermined defibrillation current waveforms to the patient.

SUMMARY OF THE INVENTION

The invention pertains to an energy transfer circuit for delivering a cardiac defibrillation pulse to a patient. The energy transfer circuit comprises an energy storage capacitor for storing an electric charge before the defibrillation pulse is delivered to the patient and electronic switch means coupled to the storage capacitor for controlling the delivery of a defibrillation pulse to a pair of electrodes disposed on the patient. A controller means is provided to control the electronic switch means. Current shunt means coupled to the electronic switch means diverts a leakage current flowing through the electronic switch means away from the pair of electrodes until the electronic switch means begins the delivery of the cardiac defibrillation pulse to the patient.

DETAILED DESCRIPTION OF THE PREFERRED EMBODIMENT

Figure 1:
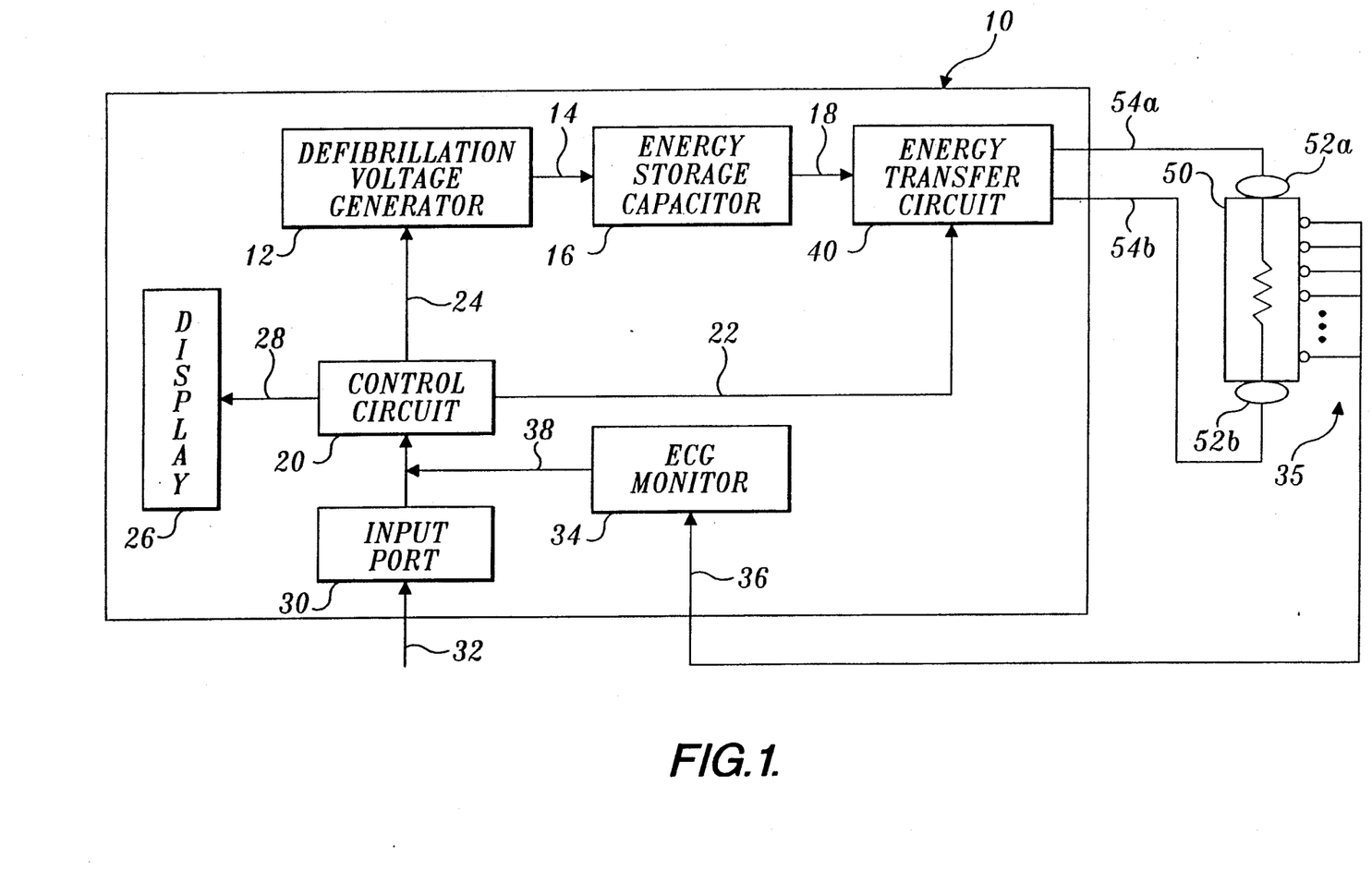
FIG. 1 is a block diagram of a cardiac defibrillator, including an energy transfer circuit according to the present invention.

FIG. 1 shows a cardiac defibrillator 10 that includes an energy transfer circuit 40 according to the present invention. A defibrillation voltage generator 12 produces a high voltage electrical signal, typically greater than 2,500 volts, which is transferred on a lead 14 to an energy storage capacitor 16. The energy storage capacitor 16 is coupled by a lead 18 to an energy transfer circuit 40. A control circuit 20, which preferably comprises a microprocessor (not separately shown), transmits a shock signal on a lead 22 to the energy transfer circuit 40. The shock signal causes the energy transfer circuit 40 to transmit a cardiac defibrillation pulse to a patient 50 which is shown as an electrical resistance. The cardiac defibrillation pulse flows from the energy storage capacitor 16 through a lead 54a to an electrode 52a, through the patient 50, and returns through an electrode 52b and a lead 54b.

An input port 30 allows an operator of the cardiac defibrillator to manually control the time at which the energy transfer circuit 40 delivers a cardiac defibrillation pulse to a patient 50 by triggering a shock signal on a lead 32. The shock signal is transmitted from the input port 30 to the control circuit 20 on leads 38. The cardiac defibrillator 10 can also automatically determine when a cardiac defibrillation pulse is needed by analyzing an electrocardiogram (ECG) signal received from the patient.

A set of ECG electrodes 35 placed on the patient 50 transmits electrocardiological signals from the patient over leads 36 to an ECG monitor 34. The ECG monitor 34 in turn transmits an ECG signal proportional to the patient's electrocardiological signals to the control circuit 20 on the leads 38. The control circuit 20 is preferably programmed to indicate to the defibrillator operator that a defibrillation pulse is needed when the occurrence or nonoccurrence of a particular portion of the ECG signal is detected, as is well known to persons skilled in the medical electronics art.

A display 26 provides the defibrillator operator with information regarding the ability of the defibrillator to deliver a cardiac defibrillation pulse, as well as displaying physiological data from the patient 50, such as heart rate, blood pressure, etc. The control circuit 20 is connected to the display 26 by leads 28.

Figure 2:
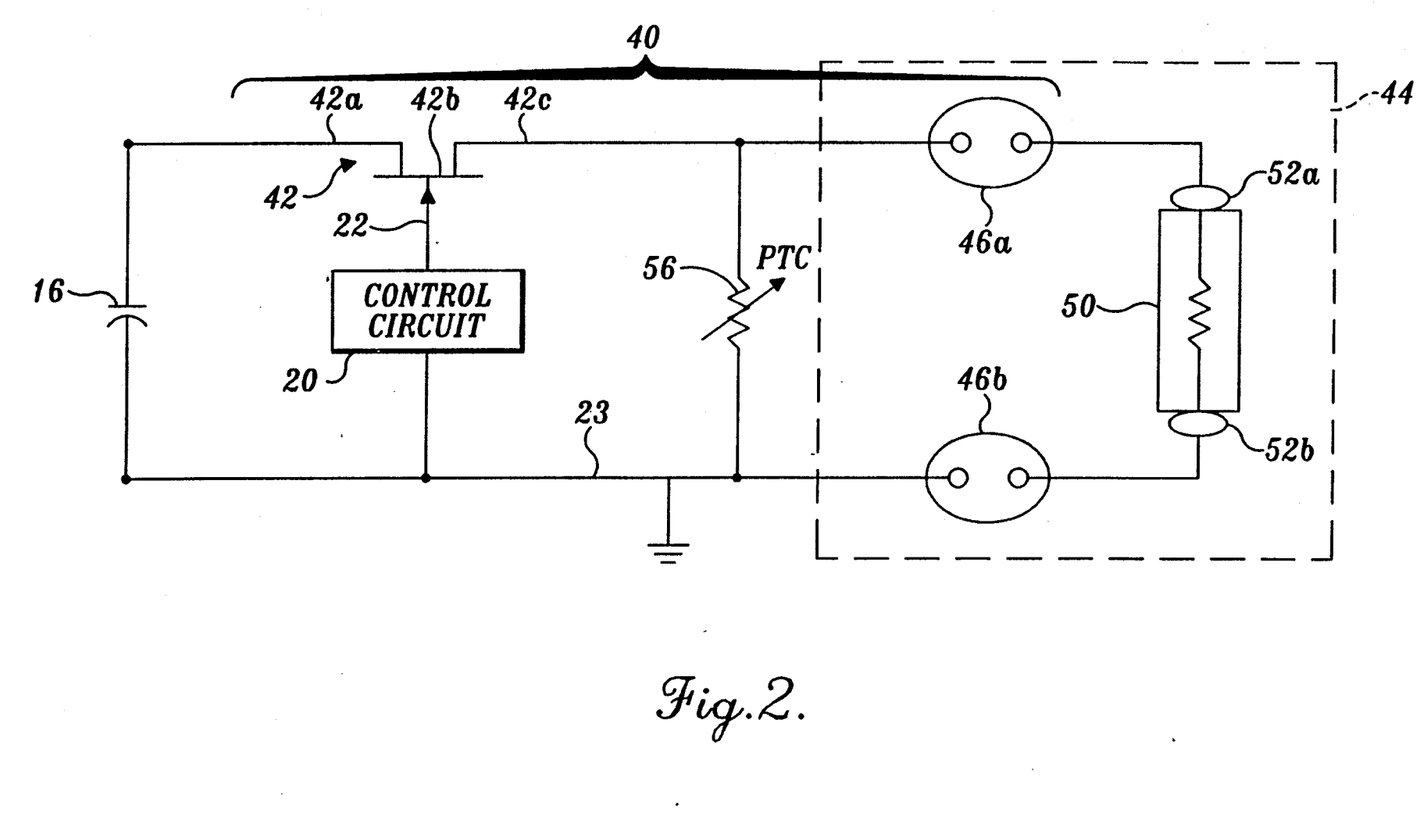
FIG. 2 is an electrical schematic diagram of a defibrillator circuit that includes a first embodiment of the energy transfer circuit according to the present invention.

FIG. 2 is a schematic diagram showing how the energy transfer circuit 40 delivers energy from the energy storage capacitor 16 to the patient 50. For the purposes of the present specification, the term "energy transfer circuit 40" is defined to include: a solid state switch 42, a current shunt 56 and a pair of spark gaps 46a and 46b of the energy transfer circuit 40 as shown in FIG. 1. Energy transfer circuit 40 is coupled to the energy storage capacitor 16 which stores the electrical energy of the cardiac defibrillation pulse before it is delivered to the patient 50. The solid state switch 42 has an input terminal 42a connected to energy storage capacitor 16, a control input terminal 42b coupled to lead 22 and an output terminal 42c connected to a patient path shown generally at 44 that includes the patient 50. A shock signal transmitted from the control circuit 20 on lead 22 causes solid state switch 42 to pass current from energy storage capacitor 16 to the patient 50. In the preferred embodiment, switch 42 comprises either a high current capacity FET transistor or a plurality of transistors (not shown) that are connected in parallel, in series, or in a series-parallel combination between the energy storage capacitor 16 and the patient 50. However, other types of solid state devices (also not shown) such as SCRs, solid state relays, or electronic switches capable of conducting high levels of current may be used for solid state switch 42.

The pair of spark gaps 46a and 46b are connected in series with the pair of patient electrodes 52a and 52b and the patient 50 to form the electrical path, which for the purposes of the present specification is called the patient path 44. Electrical current flows across the spark gaps 46a and 46b when a sufficiently high voltage signal is applied to them. As discussed above, the problem with using a solid state device for the solid state switch 42 is the fact that a certain amount of leakage current flows through the solid state switch 42 even when a defibrillation pulse is not being delivered to the patient. If this leakage current is not shunted away from the patient path 44, the patient may receive an unknown and variable level of leakage current. Therefore, the current shunt 56 is placed in parallel with the patient path 44 to divert the leakage current away from the patient path until a defibrillation pulse is delivered. Preferably, current shunt 56 has an impedance such that the potential developed across it due to the leakage current is not high enough to trigger the spark gaps 46a and 46b when the solid state switch 42 is in a nonconducting state. However, when the solid state switch 42 is operating in a conducting state, the impedance of current shunt 56 increases to become substantially greater than the impedance of the patient path 44. If the energy transfer circuit 40 is designed without spark gaps, then the impedance of the current shunt 56 should be chosen to have a value substantially less than the impedance of the patient path 44 in order to reduce the level of leakage current that flows through the patient to an acceptable level.

In the preferred embodiment, the current shunt 56 comprises a thermistor having a positive temperature coefficient, i.e., an impedance that increases with the temperature of the device. Therefore, when solid state switch 42 is operating in the nonconducting state, the current shunt 56 is cool and has a resistance low enough to prevent triggering the spark gaps 46a and 46b, thereby diverting the leakage current away from patient path 44. When switch 42 begins conducting a defibrillation pulse between energy storage capacitor 16 and the patient path 44, a high current initially flows through the current shunt 56. As a result, the temperature of the current shunt 56 rapidly rises and its impedance increases to a level substantially greater than the impedance of the patient path 44, thereby directing most of the current of the defibrillation pulse to flow through the patient path 44.

Figure 2A:
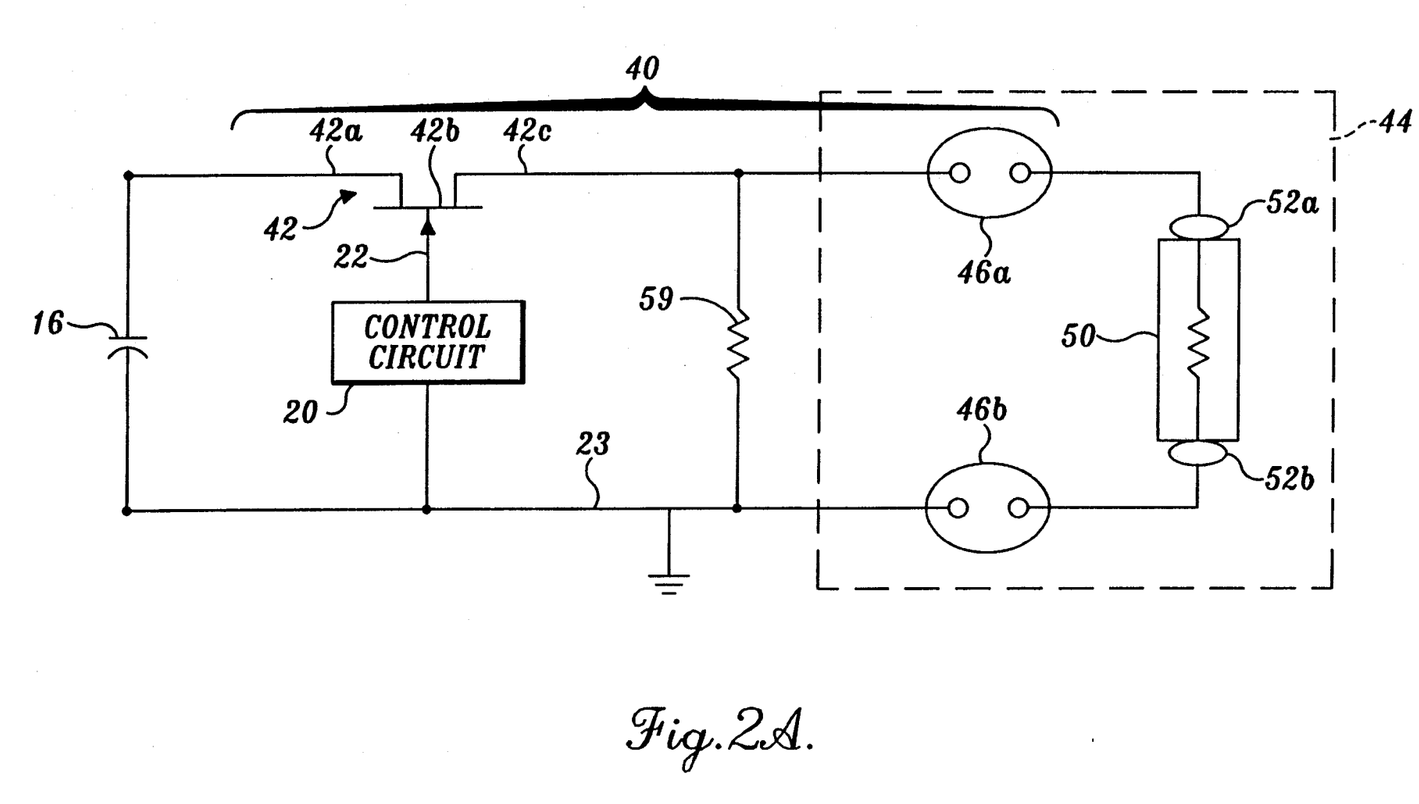
FIG. 2A is an electrical schematic diagram of a defibrillator circuit including a second embodiment of the energy transfer circuit according to the present invention.
Figure 2B:
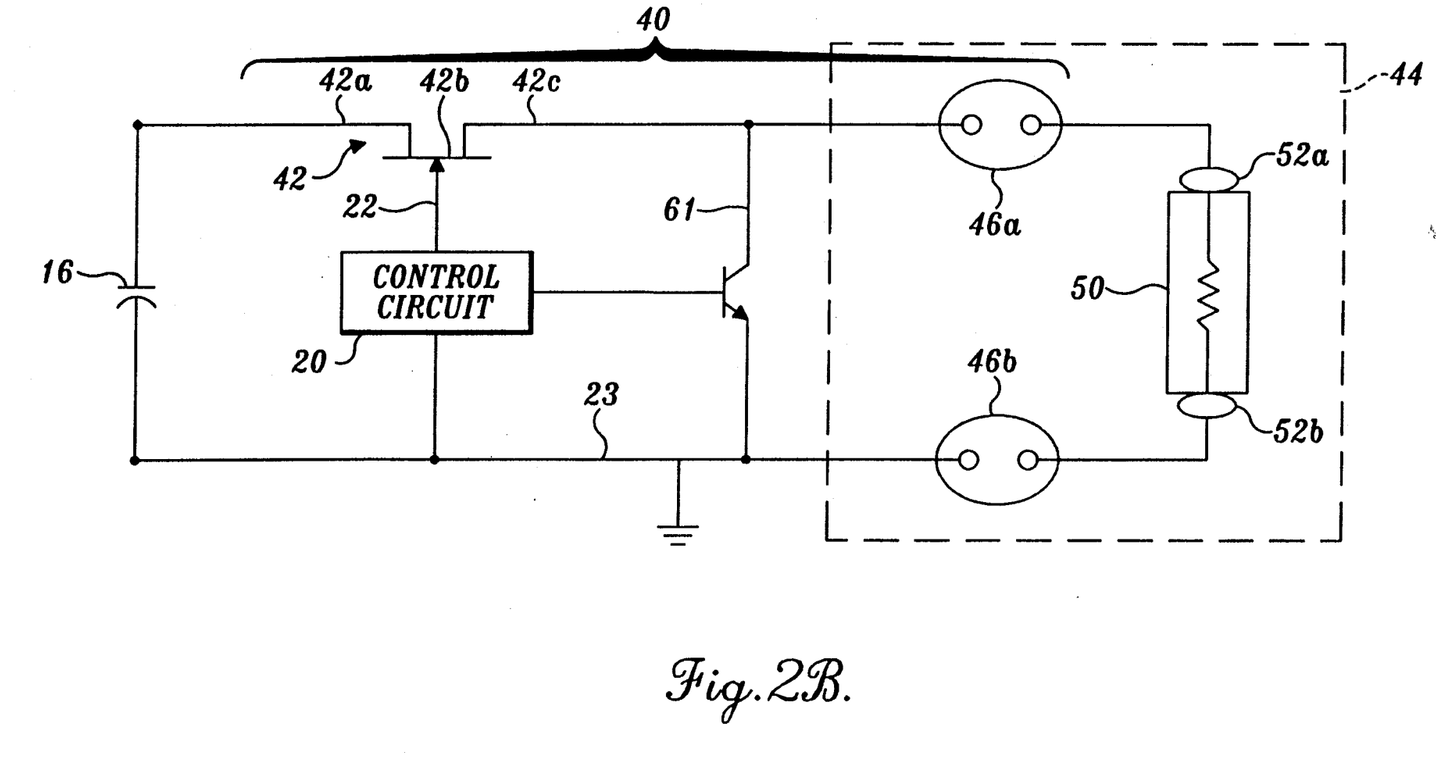
FIG. 2B is an electrical schematic diagram of a defibrillator circuit including a third embodiment of the energy transfer circuit according to the present invention.

Other types of devices may be used for the current shunt 56. For example, a fixed resistor 59, as shown in FIG. 2A could be used, as well as an inductor or an electronic component, such as a transistor 61, as shown in FIG. 2B. If a fixed resistor is used for the current shunt 56, the resistance must be chosen so that the electrical potential produced by the leakage current is less than the potential required to trigger the spark gaps. If a transistor is used, it must operate in a conducting state when solid state switch 42 is operating in a nonconducting state, and must operate in a nonconducting state when solid state switch 42 is operating in a conducting state. The problem with using a transistor for current shunt 56 is that the transistor must be able to handle voltages in the range of 2,500–3,000 volts without breaking down. The use of a thermistor for the current shunt 56 is preferable due to its ability to withstand large voltage potentials and because no additional control circuitry is required to ensure that it is conducting when switch 42 is operating in a nonconducting state.

Figure 3:
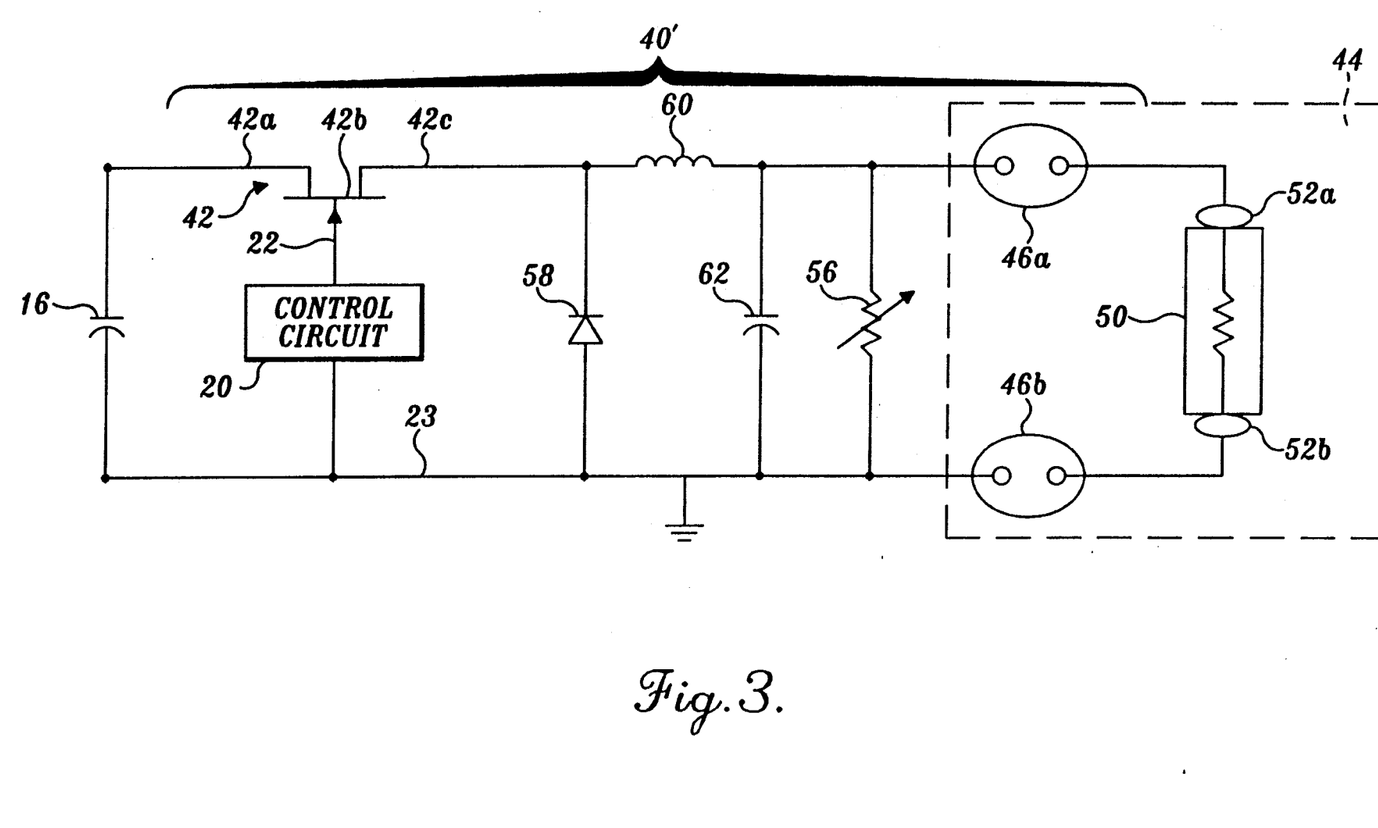
FIG. 3 is an electrical schematic diagram of a defibrillator circuit that includes a fourth embodiment of the energy transfer circuit according to the present invention.

FIG. 3 shows a fourth embodiment of the energy transfer circuit 40' according to the present invention. The fourth embodiment of the energy transfer circuit is the same as the energy transfer circuit shown in FIG. 2 except that a diode 58 connected between terminal 42c and a ground lead 23, have been added an inductor 60 connected between terminal 42c and a node 57 and a capacitor 62 connected between node 57 and the ground lead 23. Diode 58, inductor 60 and capacitor 62 serve to filter and smooth the cardiac defibrillation pulse that is delivered to the patient 50.

Figure 4:
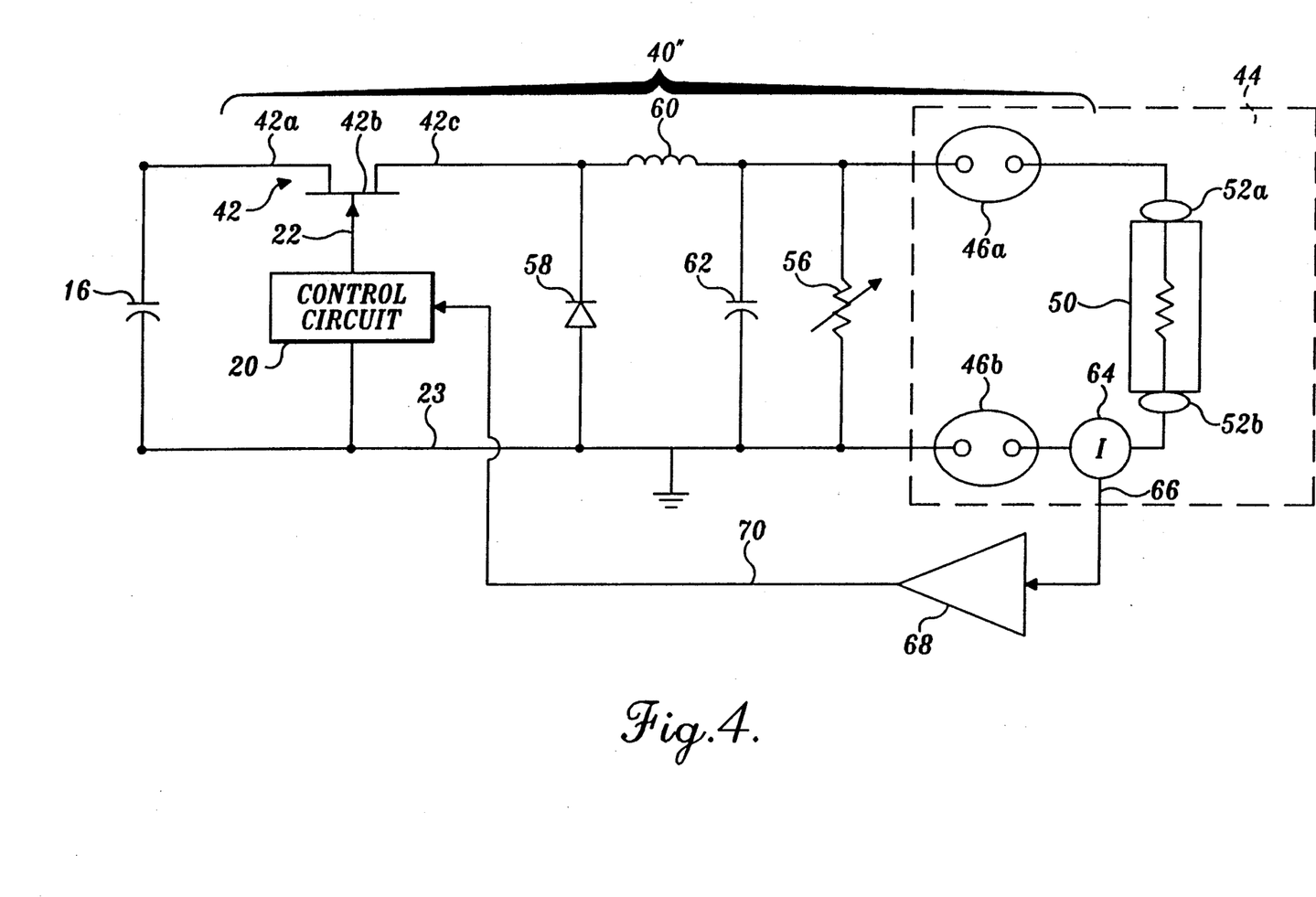
FIG. 4 is an electrical schematic diagram of a defibrillator circuit that includes an energy transfer circuit according to the present invention, including a current controlled feedback network.

FIG. 4 shows a fifth embodiment of an energy transfer circuit 40'', similar to that described in FIG. 3, except that the fifth embodiment of the energy transfer circuit includes a current sensor 64 disposed in series in the patient path 44 and an isolation amplifier 68. Current sensor 64 generates a current signal indicative of the magnitude of the current flowing in the patient path 44. The current signal is input to an isolation amplifier 68 on a lead 66. An output signal of buffer amplifier 68 is applied to the control circuit 20 on a lead 70. The control circuit 20 is programmed to control the operation of solid state switch 42 in response to the level of current flowing in the patient path 44. For example, if the current flowing in the patient path is too high, then the control circuit 20 opens the switch 42, interrupting the current flowing into the patient path. In this way, the control circuit 20 controls the amount of energy in the cardiac defibrillation pulses delivered to the patient based on the level of current flowing through the patient. As has been previously stated, if electro-mechanical relays were used for solid state switch 42, it would not be possible to regulate the amount of energy transferred to the patient 50 using such a feedback arrangement, because an electro-mechanical relay takes too long to open and close. By the time the relay could be opened, the entire cardiac defibrillation pulse would have been delivered to the patient.

Figure 5:
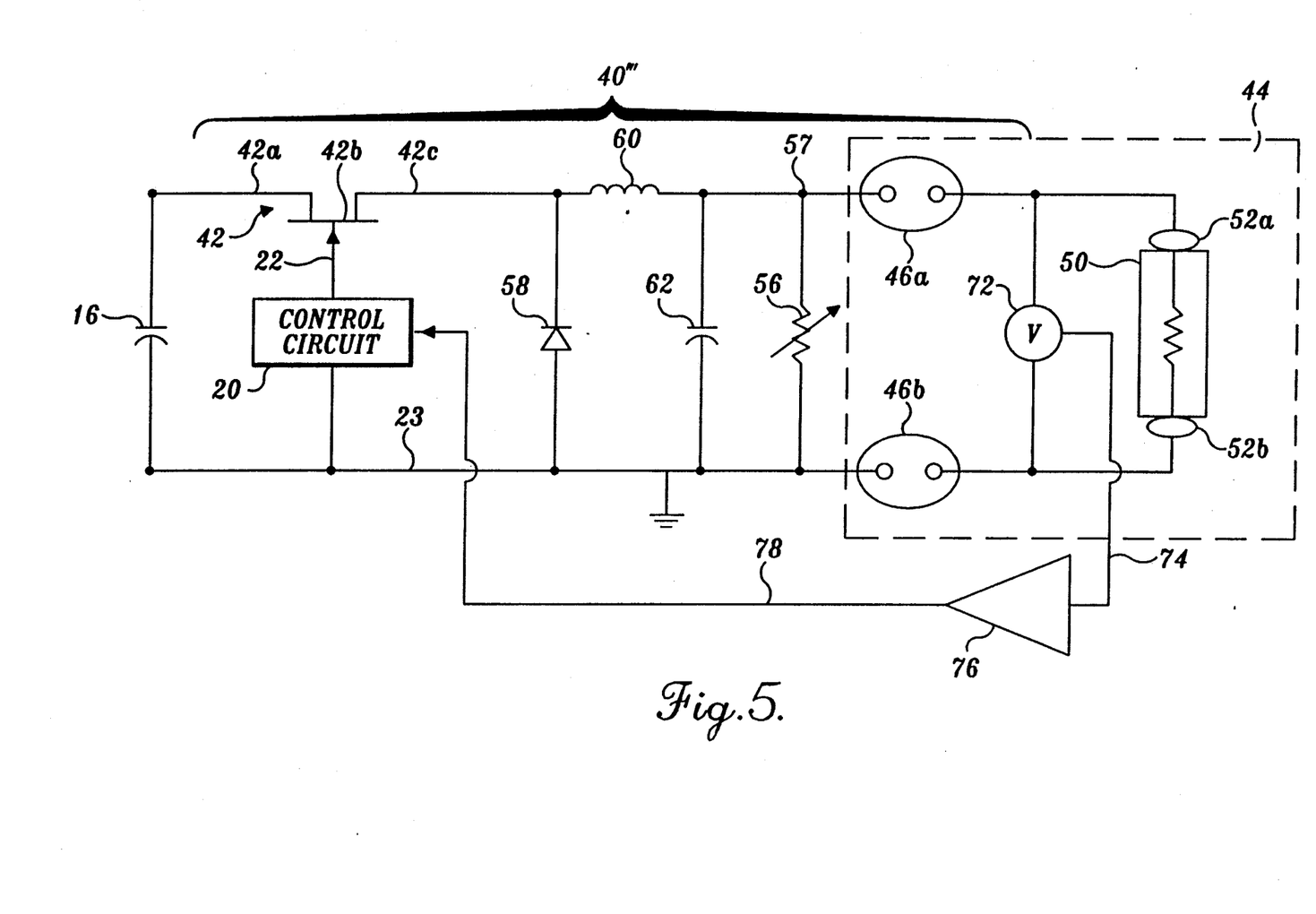
FIG. 5 is an electrical schematic diagram of a defibrillator circuit that includes an energy transfer circuit according to the present invention including a voltage controlled feedback network.

FIG. 5 shows a sixth embodiment of an energy transfer circuit 40''' according to the present invention. The sixth embodiment of the energy transfer circuit 40''' is the same as the energy transfer circuit 40'' shown in FIG. 4 except that a voltage sensor 72 and an isolation amplifier 76 have been substituted in place of the current sensor 66 and the isolation amplifier 76. The voltage sensor 72 that is connected in parallel with the electrodes 52a and 52b. The voltage sensor 72 produces a voltage signal that is proportional to the magnitude of the voltage between the patient electrodes 52a and 52b. The voltage signal is transferred to the isolation amplifier 76 on a lead 74. An output signal of isolation amplifier 76 is applied to the control circuit 20 on a lead 78. The control circuit 20 is programmed to control the transfer of energy between the energy storage capacitor 16 and the patient 50 based on the magnitude of the voltage signal produced by voltage sensor 72. By programming control circuit 20 to integrate the voltage signal received from isolation amplifier 76, an estimation can be made of the amount of energy delivered to the patient 50. If the energy delivered exceeds a predetermined level, control circuit 20 opens solid state switch 42, thereby interrupting the transfer of energy between energy storage capacitor 16 and the patient 50. Although the energy transfer circuits 40'' and 40''' show only a current sensor 64 or a voltage sensor 72, those skilled in the art will realize that an energy circuit could contain both a current and a voltage sensor. By sensing signals proportional to the level of current and the magnitude of the voltage applied to the patient, the control circuit 20 can be programmed to closely regulate the amount of electrical energy applied to the patient 50.

Figure 6:
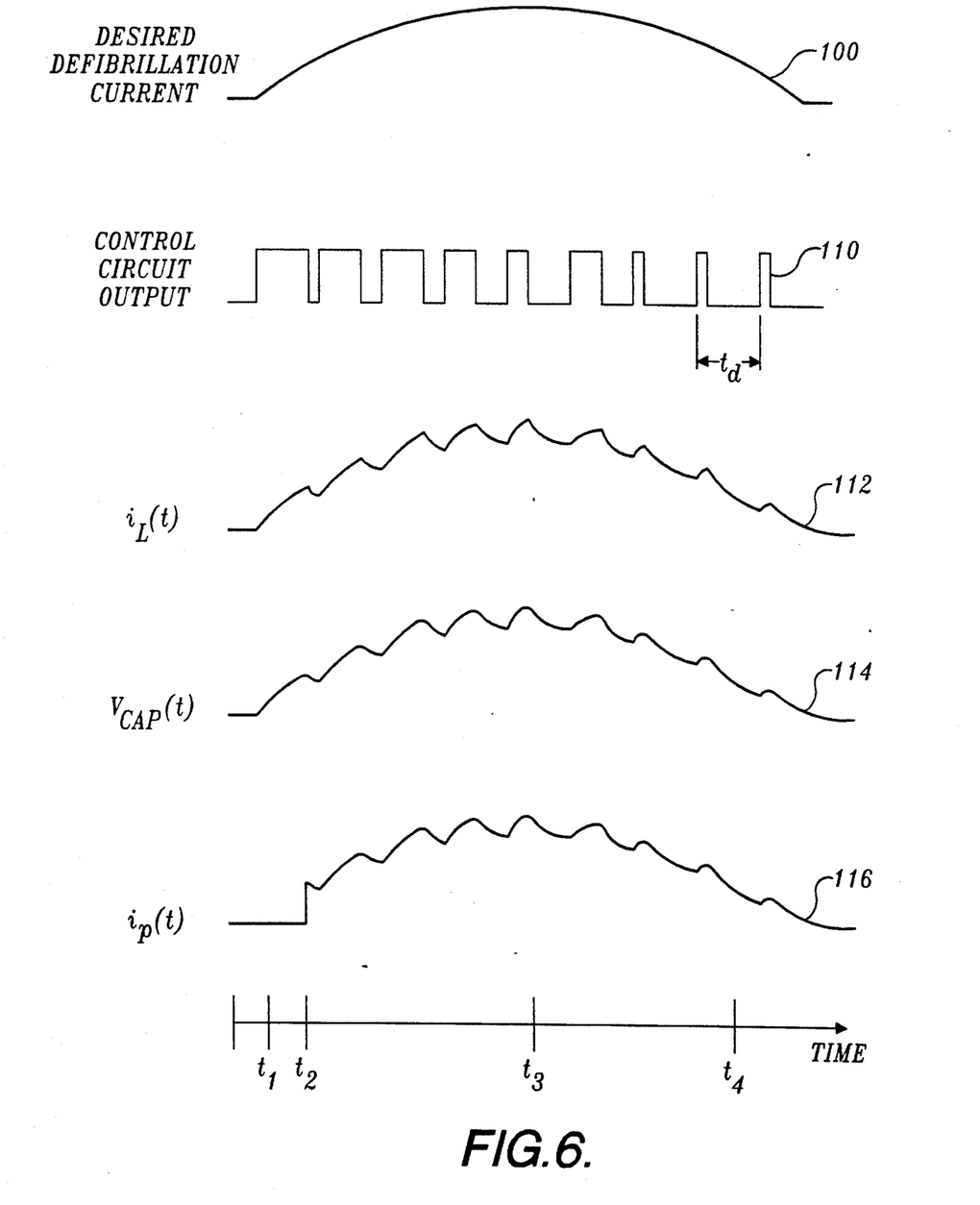
FIG. 6 is a graph showing a selected defibrillation current waveform that is delivered to a patient and other related waveforms used in the energy transfer circuit, as a function of time.

Another benefit of using a solid state device for solid state switch 42, aside from allowing feedback control of the defibrillation pulse, is the ability of the cardiac defibrillator to deliver defibrillation currents of arbitrary shape and duration to the patient. FIG. 6 shows how the energy transfer circuit, as shown in FIG. 4, operates to deliver a cardiac defibrillation waveform having a sinusoidal shape to the patient. The characteristics of a desired defibrillation waveform 100 are preferably stored in a memory circuit (not shown) that is included within the control circuit 20. Control circuit 20 operates to control the solid state switch 42 so that a defibrillation current corresponding to the shape of the desired defibrillation current 100 flows through the patient. The control circuit 20 outputs a pulse width modulated signal 110 on lead 22 that causes the solid state switch 42 to deliver pulses of energy to the patient in order to create the desired defibrillation current.

In the preferred embodiment, the maximum width of the pulses of the output signal 110 produced by the control circuit 20 is fixed at $t_d$. The control circuit compares the desired shape of current waveform 110 to the actual current, $i_p(t)$ (represented by a waveform 116) which is flowing through the patient as sensed by the current sensor 64. Control circuit 20 uses pulse width modulation to control the magnitude of current $i_p$ flowing through the patient. For example, if the actual current, $i_p$ 116 at time t, is less than the desired current in waveform 100, the pulse width of the control circuit output signal 110 is increased. If the actual current, $i_p$ 116, is greater than or equal to the desired current, then the pulse width of the output signal 110 is decreased. As shown by waveform 116, at an initial time $t_1$, the level of current flowing through the patient is zero, and the pulse width of the control circuit output signal 110 is a large percentage of the maximum pulse width $t_d$. At a time $t_2$, the voltage on the smoothing capacitor 62 (shown by waveform 114) increases to a level high enough so that the spark gaps 46a and 46b begin conducting and current begins to flow through the patient. At a time $t_3$, the actual current $i_p$ 116 flowing through the patient and the desired defibrillation current 100 are at a maximum, so the control circuit 20 begins to decrease the pulse width of the pulses in output signal 110.

Finally, at a time $t_4$, the desired defibrillation current is near a minimum, so that the width of the pulses in the control circuit output signal 110 are also a minimum. As can be seen, the shape of the actual current $i_p$ 116 flowing through the patient closely approximates the shape of the desired defibrillation current waveform 100. The fluctuations shown in the diagram are for illustrative purposes and more closely approximate the desired waveform in the actual instrument. Although the above description has been made with respect to the energy transfer circuit shown in FIG. 4, those skilled in the art will realize that the circuit shown in FIG. 5 operates to deliver a desired defibrillation waveform in nearly the same manner with the exception that the energy transfer circuit in FIG. 5 uses voltage controlled feedback instead of current controlled feedback. Using the feedback arrangement shown in either FIG. 4 or FIG. 5, it is possible to deliver a cardiac defibrillation current of almost any shape to the patient. For instance, the shape of the defibrillation current may be continually adjusted to maintain the current at a specific level throughout the duration of the defibrillation pulse. This technique, which is known as "current dose" defibrillation, is not possible when electro-mechanical relays are used due to the slow response time of such relays. Additionally, waveshapes may be driven to either polarity by the addition of a bridge network (not shown) in the output stage.

Although the present invention has been described with respect to the preferred embodiments, those skilled in the art will realize that changes could be made without departing from the spirit and scope of the invention. Therefore, it is intended that the scope of the invention be determined solely by reference to the following claims.

The embodiments of the invention in which an exclusive property or privilege is claimed are defined as follows:

1. A defibrillator circuit for delivering a cardiac defibrillation pulse to a pair of defibrillation electrodes that are applicable to a patient, comprising:
   an electrical energy source for supplying electrical energy required to defibrillate the patient;
   an energy source means for storing the electrical energy before the cardiac defibrillation pulse is delivered to the patient;
   electronic switch means coupled to the energy storage means for controlling the delivery of the cardiac defibrillation pulse from the energy storage means to the pair of defibrillation electrodes;
   controller means for controlling the electronic switch means; and
   current shunt means coupled to the electronic switch means, for shunting a portion of any leakage current that flows through the electronic switch means until the controller means deliver the cardiac defibrillation pulse to the pair of defibrillation electrodes.

2. The energy transfer circuit as in claim 1, wherein the electronic switch means comprises at least one transistor connected in series between the energy storage capacitor and the pair of defibrillation electrodes.

3. The energy transfer circuit as in claim 1, wherein the current shunt means comprises a current shunt resistor that is disposed in parallel with the pair of defibrillation electrodes, wherein the current shunt resistor has a positive temperature coefficient.

4. The energy transfer circuit as in claim 1, wherein the current shunt means comprises a thermistor.

5. The energy transfer circuit as in claim 1, wherein the electronic switch means comprises at least one field effect transistor connected in series between the energy storage means and the pair of defibrillation electrodes.

6. The energy transfer circuit as in claim 1, further comprising:
   a current sensor connected in series with the pair of defibrillation electrodes, wherein the current sensor generates a current signal indicative of the level of a defibrillation current flowing through the patient, and wherein the controller means is connected to receive the current signal and controls the electronic switch means in response to the current signal.

7. The energy transfer circuit as in claim 1, further comprising:
   a voltage sensor that generates a voltage signal proportional to the magnitude of the voltage of the defibrillation pulse applied to the patient, wherein the controller means is connected to receive the voltage signal and controls the electronic switch means in response to the voltage signal.

8. The energy transfer circuit as in claim 1, wherein the current shunt means comprises a transistor that operates in an ON state and an OFF state, such that before the defibrillation pulse is delivered to the patient, the transistor operates in the ON state in order to shunt the leakage current, and operates in the OFF state when the cardiac defibrillation pulse is being delivered to the patient.

9. The energy transfer circuit of claim 1, wherein the current shunt comprises a resistor having a fixed resistance.

10. The energy transfer circuit of claim 1, further comprising:
    a current sensor coupled to the controller means that generates a current signal indicative of the level of current flowing through the patient;
    a voltage sensor coupled to the controller means that generates a voltage signal indicative of the voltage of the defibrillation pulse applied to the patient;
    wherein the controller means controls the electronic switch means to regulate an amount of electrical power delivered to the patient as a function of the current and voltage signals.

11. A cardiac defibrillator circuit for delivering a cardiac defibrillation pulse to a patient through a pair of defibrillation electrodes comprising:
    an electrical energy source for supplying electrical energy to defibrillate the patient;
    an energy storage means for storing the electrical energy before the cardiac defibrillation pulse is delivered to the patient;
    a switch disposed between the energy storage means and the pair of defibrillation electrodes, wherein the switch is nonconducting when a defibrillation pulse is not being delivered to the patient and conducting at least a portion of the time while the cardiac defibrillation pulse is being delivered to the patient;
    a switch controller for controlling the switch; and
    a current shunt that diverts a portion of a leakage current flowing through the switch when it is nominally nonconducting away from the pair of defibrillation electrodes.

12. The energy transfer circuit as in claim 11, further comprising a pair of spark gaps disposed in series with the pair of defibrillation electrodes, wherein the current shunt is disposed in parallel with the pair of spark gaps and wherein the current shunt has a variable impedance that is less than the impedance of the pair of spark gaps, the pair of defibrillation electrodes and the impedance of the patient when the switch is nonconducting and greater than the impedance of the pair of spark gaps, the pair of defibrillation electrodes and the impedance of the patient when the switch is conducting.

13. The energy transfer circuit as in claim 12, wherein the current shunt comprises a thermistor having a positive temperature coefficient.

14. The energy transfer circuit as in claim 12, wherein the switch comprises at least one transistor connected in series between the energy storage capacitor and the pair of defibrillation electrodes.

15. The energy transfer circuit as in claim 12, further comprising: an inductor disposed in series between the switch and the pair of defibrillation electrodes and a smoothing capacitor connected in parallel with the current shunt.

16. The energy transfer circuit as in claim 11, further comprising a current sensor coupled to the switch controller for generating a current signal proportional to the magnitude of a defibrillation current flowing through the pair of defibrillation electrodes.

17. The energy transfer circuit as in claim 16, wherein the switch controller is connected to receive the current signal and controls the switch in response to the current signal.

18. The energy transfer circuit as in claim 11, further comprising a voltage sensor coupled to the switch controller for generating a voltage signal proportional to the magnitude of the voltage of the defibrillation pulse applied to the patient.

19. The energy transfer circuit as in claim 18, wherein the switch controller is connected to receive the voltage signal and controls the switch in response to the voltage signal.

20. A cardiac defibrillator circuit for delivering a cardiac defibrillation pulse to a patient comprising:
  a source of electrical energy;
  energy storage means for storing energy received from the source of electrical energy;
  a spark gap;
  a pair of defibrillation electrodes that are attachable to the patient;
  a patient path that includes the series connection of the spark gap, the pair of defibrillation electrodes and the patient through which the cardiac defibrillation pulse is delivered to the patient;
  switch means for selectively transferring energy from the energy storage means to the patient path; and
  a shunt path disposed in parallel with the patient path for diverting any leakage current flowing through the switch means away from the patient path until the cardiac defibrillation pulse is delivered to the patient, said shunt path having an impedance that is less than the impedance of the patient path such that an electrical potential developed across the shunt path by the leakage current is less than a potential required to cause the spark gap to conduct electrical current.

21. The energy transfer circuit as in claim 20, wherein the spark gap is connected between the energy storage means and the pair of defibrillation electrodes.

* * * * *

UNITED STATES PATENT AND TRADEMARK OFFICE
CERTIFICATE OF CORRECTION

PATENT NO. : 5,222,492

DATED : June 29, 1993

INVENTOR(S) : C. B. Morgan et al.

It is certified that error appears in the above-identified patent and that said Letters Patent is hereby corrected as shown below:

| COLUMN | LINE | |
|---|---|---|
| 5 | 12 | "lead 23, have been added" should read --lead 23 have been added,-- |
| 7 | 29 | "source" should read --storage-- |

Signed and Sealed this

Fifteenth Day of March, 1994

Attest:

BRUCE LEHMAN

*Attesting Officer*    *Commissioner of Patents and Trademarks*